(12) United States Patent
Minakawa

(10) Patent No.: US 6,537,543 B1
(45) Date of Patent: Mar. 25, 2003

(54) INTESTINAL ACTIVATION FOOD USING NATTO POWDER

(75) Inventor: Hiromichi Minakawa, Mito (JP)

(73) Assignee: Unicafe Inc., Tokyo (JP)

( * ) Notice: Subject to any disclaimer, the term of this patent is extended or adjusted under 35 U.S.C. 154(b) by 0 days.

(21) Appl. No.: 09/716,093

(22) Filed: Nov. 17, 2000

(30) Foreign Application Priority Data

Sep. 14, 2000 (JP) ........................................ 2000-279062

(51) Int. Cl.$^7$ .................. A01N 63/00; A61K 35/78; A23L 1/36; A23C 17/00
(52) U.S. Cl. ...................... 424/93.4; 424/115; 424/780; 424/451; 424/464; 426/43; 426/52; 426/71; 426/629
(58) Field of Search ................ 424/115, 93.4, 424/780, 451, 464; 426/43, 2, 71, 52, 72, 629, 648, 656, 658, 443

(56) References Cited

U.S. PATENT DOCUMENTS

| | | | | |
|---|---|---|---|---|
| 4,110,477 A | * | 8/1978 | Naruse et al. | |
| 6,022,580 A | * | 2/2000 | Akatsuka | |

FOREIGN PATENT DOCUMENTS

| | | | |
|---|---|---|---|
| JP | 58111657 | * | 7/1983 |
| JP | 60214740 | * | 10/1985 |
| JP | 63141552 | * | 6/1988 |
| JP | 12566363 | * | 10/1989 |
| JP | 3143372 | * | 6/1991 |
| JP | 6007156 | * | 1/1994 |
| JP | 8214833 | * | 8/1996 |
| JP | 10305268 | * | 11/1998 |
| JP | 11018712 | * | 1/1999 |

OTHER PUBLICATIONS

Dorland's Illustrated Medical Dictionary, 27th ed., 1988. p. 1568.*
Jones et al. Introductory Biology. 1977. Publisher: John Wiley & Sons, Inc. NY, NY, p. 597.*

* cited by examiner

*Primary Examiner*—Christopher R. Tate
(74) *Attorney, Agent, or Firm*—Dilworth & Barrese LLP

(57) ABSTRACT

The purpose of the present invention is to offer an intestinal activation food product containing natto powder that delivers the natto bacteria live.to the intestines and produces an adequate intestinal regulating effect by enhancing the mitotic growth of the natto bacteria delivered to the intestines and, furthermore, a product that is easy to take without causing the offensive smell peculiar to natto during storage. For this reasons, the intestinal activation food product containing natto powder in accordance with this invention is a uniform blend obtained by blending to 15 wt. % of natto powder containing the natto bacteria with 50 wt. % of lactose as the growth factor substance, 30 wt. % of 300 mesh particle size coffee powder as the porous substance and 5 wt. % of sporophyte-containing lactic acid bacilli as the germination inducing substance and filling 0.5 g of this mixture into a hard capsule.

10 Claims, No Drawings

INTESTINAL ACTIVATION FOOD USING NATTO POWDER

BACKGROUND OF THE INVENTION

1. Field of the Invention

The present invention relates to an intestinal activation food product using natto powder, and more specifically, to an intestinal activation food product containing in a readily digestible form natto bacteria which are contained in natto, a food well known for its health values to the human body.

2. Description of the Related Art

Some 100 species of intestinal bacteria are said to be present in the intestinal tract at a level of around a hundred trillion organisms and their different functions include the synthesis of hormones and vitamins and the formation of vitamins and enzymes, minerals and proteins as well as the regulation of intestinal activity and the maintenance of human life. Among these intestinal bacteria there are some that are beneficial to human health and some that are injurious, the former being known as Good Bacteria (effective or beneficial bacteria) and the latter as Bad Bacteria, with the natto bacteria being representative of the Good Bacteria.

Natto bacteria, a variety of the hay bacteria, are used in the making of natto by fermenting soybeans and breaking them down. They have a variety of effects, including a powerful antibacterial action that controls the growth of Bad Bacteria entering the body and killing them, an enhancement in digestive food absorption by controlling the action of the intestinal decomposing bacteria that are the cause of constipation and diarrhea, an enhancement of physical stamina, a carcinostatic effect, the prevention of blood pressure rises, the prevention of thrombus formation, the prevention of osteoporosis, and improvement of pancreatitis.

A variety of foods using the beneficial natto bacteria directly or as a raw material have already been proposed until the present.

Many of the natto bacteria using foods proposed as of the present, however, are produced using natto kinase prepared from natto as the raw material and/or the products formed by natto bacteria. Yet, these foods do not achieve the full effect or effects inherent in natto bacteria.

Thus, a large number of natto bacteria are already living bacteria when eating natto in the normal manner. In an acidic environment below pH 5, however, natto bacteria have the characteristic property that they will cease to be active and enter a dormant phase. They will thus cease to be active under the influence of the stomach acids and will be eliminated by excretion as it takes some time for germination to occur.

Even when the natto bacterium has reached the intestines it will thus not be retained in the intestinal tract and be eliminated from the body without adequately exerting its beneficial action which may be to enhance the activity of the Good intestinal bacteria or to produce new nutrients unless it can immediately begin to sprout from the sporangial state and grow by mitosis.

However, the consumption of foods made from natto is somewhat shunned because of the potent smell that is peculiar to natto. Further, the sprouting of natto bacteria in the sporangial state causes the smell that is peculiar to natto. As a result, natto has to be stored at low temperature at which sprouting cannot take place and it is normally difficult to store natto for a long time.

This invention purports to resolve or overcome these drawbacks and its aim is to deliver the natto bacteria to the intestines in the live form and to have the natto bacteria delivered to the intestines produce their intestinal regulating effect to the full by increasing their mitotic growth, while, at the same time, offering an intestinal activation food with natto bacteria in an easy-to-eat form without the offensive smell peculiar to natto during storage.

SUMMARY OF THE INVENTION

The present invention brings about an adequate intestinal regulating effect by imparting to the natto bacteria capable of producing an intestinal activation effect their own food and habitat and causing the natto bacteria in the intestines to proliferate by mitotic growth more effectively by simultaneously delivering their food and living environment to the intestine in which they are active, as compared with the effect of natto bacteria obtaining their nutrients directly in the intestines and from the food in the body.

DESCRIPTION OF THE PREFERRED EMBODIMENTS

The present invention relates to an intestinal activation food containing in an integral compound as its ingredients at least natto powder which contains the natto bacteria, a growth factor (GF) substance used as the food to promote mitotic growth of the natto bacteria and a porous substance as the habitat for the natto bacteria to grow and proliferate. In this manner, the natto bacteria use the growth factor substance for food, the porous material as the habitat to permit mitotic growth under these stable, desirable conditions.

The phase "at least" employed in this context should be interpreted to mean that the natto powder, growth factor substance and porous substance are all essential ingredients that must be present in the intestinal activation food according to the present invention. It is therefore admissible that other components apart from these essential ingredients may be present when required. Thus, for example, it may be possible without problem to include sweetening and/or coloring agents, flavors, tonics or other food additives as well as the germination inducing substances for natto bacteria described below.

The natto bacteria according to the present invention may also be sporophytes in the sporangial stage. They will therefore be delivered to the intestines without being impaired or impeded by the action of the stomach acid so that virtually all of the ingested natto bacteria will proliferate by mitotic growth. When natto bacteria are ingested in the fasted or hungry condition they will not be significantly affected by the action of the stomach acid and pass into the intestinal tracts with water where they can sprout and grow easily at the intestinal temperature.

Furthermore, the growth factor substance according to the present invention may be sugar, soy protein, lipid or vitamin H. Their presence enables the natto bacteria to imbibe without difficulty effective growth factor substances as their food.

Moreover, the porous substance in accordance with the present invention may consist of roasted coffee bean powder. In its presence, the natto bacteria are not only able to achieve a dramatic growth but the use of the coffee bean powder also holds promise of a stench-controlling effect that subdues the offensive smell peculiar to natto with the fragrance of coffee beans.

Further, the present invention may also include as an integral part the further addition of a germination inducing substance for the natto bacteria when necessary. The preferred germination inducing substance is lactic bacillus. In the presence of the germination inducing substance, the sporophytic natto bacteria in the sporangial stage delivered to the intestines are stimulated to induce sprouting with the result of the subsequent formation of a concatenation of germination.

Further, according to this invention the above components consisting of the natto powder, the growth factor substance and the porous substance as well as the germination inducing substance which may be added when necessary may be united either in a capsule or tablet. In this manner, the natto bacterium containing intestinal activation food is made easy to take and ingest.

In the case of the above capsule, the product may be a preparation obtained by filling the ingredients into the capsule or by coating them with the capsule substrate. In the case of the above tablet or pill, the product may be produced by forming each of the ingredients to a particular shape and drying them to obtain a pill produced by a wet process or by compressing each of the ingredients and forming them by compression to a certain shape to obtain a compressed pill. It may also be possible to coat the capsule or table (pill) in accordance with the present invention with a drug coating prepared, for example, from white sugar (cane sugar) or chocolate as required mainly in order to control the target point of the above ingredients in the body and to control their effect by imparting an intestinal solubility property to the ingredients.

The ratio at which the ingredients can be blended into one may be calculated on the basis of the admixture of natto powder in such a manner that if the addition of a germination inducing substance is required, the natto powder quantity may be 5–30% by weight, the growth factor substance 10–74% by weight, the porous substance 20–50% by weight and the germination inducing substance 1–10% by weight.

The following explanations refer to embodiments of the present invention.

The intestinal activation food product containing natto powder in accordance with this invention is a uniform blend obtained by blending to 15 wt. % of natto powder containing the natto bacteria with 50 wt. % of lactose as the growth factor substance, 30 wt. % of 300 mesh particle size coffee powder as the porous substance and 5 wt. % of sporophyte-containing lactic acid bacilli as the germination inducing substance and filling 0.5 g of this mixture into a hard capsule.

In order to check that the intestinal activation food product containing natto powder in the above capsular form in accordance with this invention has an intestinal regulating effect, the aforesaid intestinal activation food product containing natto powder was administered and the resulting changes in body condition observed. One capsule of the intestinal activation food product containing natto powder was taken with water on an empty stomach immediately after getting up each morning. The following changes in body conditions were observed as a result. First, the offensive smell peculiar to natto was total absent when taking the preparation. On the following day, the stool and gas excreted from the body had lost their offensive smell and no unpleasant smell was noted in the toilet after defecation. The stool had an ideal consistency, being neither too hard nor too soft, and was discharged immediately after being seated on the toilet seat. Flatulence and with stomach rumbling was also contained.

Stool is normalized even in people apt to develop constipation during travel at the destination when regular passage each day will take place when taken in the morning of the travel day. Persons with essential constipation such as persons who will not have a motion even after taking a constipation drug in the prescribed dose or persons with intestinal tract problems, began to have a regular daily motion from the second or third day. It does appear that a motion will be passed only on alternate days unless the daily food intake is a minimum of 1000 g.

Further, to determine next whether the intestinal activation food product containing natto powder in accordance with the present invention can be stored at normal temperature for a long time without the occurrence of the stench peculiar to natto at the time of ingestion, a preparation with coffee powder and one without coffee powder was prepared and stored together at 25 degrees C to perform a stench detection test. As a result, it was possible to detect the offensive smell peculiar to natto from the third day in the preparation made without coffee powder. In contrast, no natto smell was detected in the preparation made with coffee powder even after 30 days' storage or longer when only the coffee aroma was detectable.

According to the afore-described invention, it is possible to impart natto bacteria which have an activating effect in the intestines with a sufficient intestine regulating action by endowing them with their own food consisting of a growth factor substance and their own habitat consisting of a porous substance to facilitate nutrient ingestion and mitotic growth.

Further, in accordance with the present invention it is possible to deliver the natto bacteria to the intestines without being damaged by the stomach acid by using the natto bacteria as a sporophyte in the sporangial stage. This promises a substantial effect due to the dramatic growth in a short time arising from the fact that practically all of the ingested natto bacteria are involved in mitotic growth.

Furthermore, in accordance with the present invention it is possible not only to achieve a major effect associated with the dramatic growth in the porous material due to the use of roasted coffee bean powder as the porous substance but also to control or curtail the offensive smell peculiar to natto with the pleasing fragrance of coffee beans. Moreover, the preparation can also be carried in person as the offensive smell peculiar to natto does not occur even during prolonged storage at normal temperatures.

Moreover, the pleasant aroma of coffee beans after the ingestion of the coffee bean powder will mask the offensive smell erupting from the stomach and the malodor released from the stomach need no longer cause concern when conversing with other people.

Furthermore, in accordance with this invention it is possible to achieve a major effect due to the dramatic growth of the natto bacteria in a short time by adding a substance with a germination inducing effect on natto bacteria as required to promote germination of the natto sporophytes delivered to the intestines in the sporangial form.

Furthermore, in accordance with the invention, it is possible to facilitate the taking of intestinal activation food products using natto powder without detriment to the germination and growth of the natto bacteria by compounding the above natto powder, growth factor substance, and porous substance as well as the germination inducing substance when required by filling the integral blend into a capsule used for filling drugs and capable of dissolving in the stomach.

What is claimed is:

1. Intestinal activation food product comprising, in integral form,

Natto powder which comprises Natto bacteria, a growth factor (GF) constituting a nutrient medium for said Natto bacteria, and a porous material constituting a habitat for proliferating said Natto bacteria, wherein said Natto bacteria are in a form of spores capable of germinating, said growth factor is selected from the group consisting of sugar, soy bean protein, lipid and vitamin H, and mixtures thereof, and said porous material is roasted coffee bean powder.

2. The food product of claim 1, additionally comprising a germination-inducing substance for said Natto bacteria and in integral form with said other components.

3. The food product of claim 2, wherein said germination-inducing substance is lactic acid bacillus.

4. The food product of claim 1, integrally formed in the shape of a capsule or tablet.

5. The food product of claim 2, integrally formed in the shape of a capsule or tablet.

6. The food product of claim 3, integrally formed in the shape of a capsule or tablet.

7. The food product of claim 2, comprising 5 to 30 weight percent of said Natto powder, 10 to 74 weight percent of said growth factor, 20 to 50 weight percent said coffee powder, and 1 to 10 weight percent of said germination-inducing substance.

8. The food product of claim 7, wherein said components are mixed and integrally formed into a capsule or tablet.

9. The food product of claim 7, comprising about 15 weight percent of said Natto powder, about 50 weight percent of lactose as said growth factor material, about 30 weight percent of said coffee powder of 300 mesh particle size as said porous material, and about 5 weight percent of spore-forming lactic acid bacillus as said germination-inducing substance, with all said components being mixed and integrally formed into a capsule or compounded into a tablet.

10. Intestinal activation food product comprising, in integral form,

Natto powder including Natto bacteria, a growth factor material serving as a habitat for said Natto bacteria, a porous material constituting a habitat for proliferating said Natto bacteria, wherein said porous material is roasted coffee bean powder, and said Natto powder, growth factor, and roasted coffee bean powder are integrally formed into a capsule or compounded into a tablet.

* * * * *